United States Patent
Böing et al.

(10) Patent No.: US 7,747,406 B2
(45) Date of Patent: Jun. 29, 2010

(54) METHOD FOR TESTING AND CONTROLLING WORKFLOWS IN A CLINICAL SYSTEM AND/OR COMPONENTS THEREOF

(75) Inventors: Dieter Böing, Erlangen (DE); Gregor Malischnig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 992 days.

(21) Appl. No.: 11/478,759

(22) Filed: Jun. 29, 2006

(65) Prior Publication Data

US 2007/0050759 A1    Mar. 1, 2007

(30) Foreign Application Priority Data

Jul. 1, 2005  (DE) ..................... 10 2005 031 245

(51) Int. Cl.
G06F 19/00  (2006.01)
(52) U.S. Cl. ................ 702/108; 703/6; 703/1; 705/2; 705/3; 705/7; 718/104; 717/124; 700/214; 600/443; 382/128
(58) Field of Classification Search ............... 702/108; 703/1, 6; 705/2, 3, 7, 9, 10; 718/104; 717/135, 717/124; 700/15, 17, 214; 600/300, 437, 600/443; 707/1; 382/128, 229
See application file for complete search history.

(56) References Cited

U.S. PATENT DOCUMENTS

| | | | |
|---|---|---|---|
| 5,740,090 A | | 4/1998 | Steinbuch et al. |
| 5,781,442 A | * | 7/1998 | Engleson et al. ............ 700/214 |
| 6,532,483 B1 | | 3/2003 | Wendel et al. |
| 6,697,765 B2 | | 2/2004 | Kuth |
| 7,533,008 B2 | * | 5/2009 | Mangino et al. ............... 703/6 |
| 2001/0044761 A1 | | 11/2001 | Berger et al. |
| 2002/0099571 A1 | * | 7/2002 | Waku et al. .................... 705/2 |
| 2002/0128870 A1 | * | 9/2002 | Whitson ........................ 705/3 |
| 2003/0050794 A1 | * | 3/2003 | Keck .............................. 705/2 |
| 2003/0065669 A1 | * | 4/2003 | Kahn et al. ................. 707/100 |
| 2003/0191374 A1 | | 10/2003 | Tsao |
| 2004/0034857 A1 | * | 2/2004 | Mangino et al. ............ 718/104 |

(Continued)

FOREIGN PATENT DOCUMENTS

DE  195 30 095  2/1997

(Continued)

*Primary Examiner*—Carol S Tsai
(74) *Attorney, Agent, or Firm*—Schiff Hardin LLP

(57) ABSTRACT

In a method to test a clinical and/or medical-technical system and a method for controlling medical-technical examination workflows in a clinical and/or medical-technical system, medical examination workflows in the appertaining system are simulated. For this purpose, a process workflow plan is selected from a number of process workflow plans dependent on an examination task, each of the process workflow plans including a number of linked process units with which system component of the system are respectively associated. Each process workflow plan also includes an input parameter set, an output parameter set and a transfer function that is dependent on the examination task and/or the associated system component. Respective output parameter values and/or performance data for the individual process units are then determined from a number of input parameter values for the appertaining process units on the basis of the transfer function. Respective output parameter values of a process unit are used as input parameter values for a subsequent process unit within the process workflow plan.

20 Claims, 10 Drawing Sheets

U.S. PATENT DOCUMENTS

| | | | |
|---|---|---|---|
| 2004/0230404 A1* | 11/2004 | Messmer et al. | 703/1 |
| 2004/0254465 A1* | 12/2004 | Sano et al. | 600/443 |
| 2005/0118557 A1 | 6/2005 | Sumner, II et al. | |
| 2006/0031112 A1* | 2/2006 | Barth et al. | 705/10 |
| 2007/0061176 A1* | 3/2007 | Gress et al. | 705/7 |
| 2007/0106633 A1* | 5/2007 | Reiner | 707/1 |
| 2007/0203744 A1* | 8/2007 | Scholl | 705/2 |
| 2007/0282581 A1* | 12/2007 | Mangino et al. | 703/6 |
| 2007/0288212 A1* | 12/2007 | Messmer et al. | 703/6 |

FOREIGN PATENT DOCUMENTS

| | | |
|---|---|---|
| WO | WO 03/094087 | 11/2003 |

* cited by examiner

FIG 6

Display unit UF

| Nr. | Process unit | UA | ZD t=Const. | DV V=Const. |
|---|---|---|---|---|
| 1 | VRT | always | t=1 min | V=100 MB |
| 2 | CAD | Intestine | t=5 min | V=50 MB |
|  |  | Abdominal aorta aneurysm | t=3 min | V=70 MB |
| 3 | Bone removal | always | t=1.5 min | V=0 |
| ... | ... | ... | ... | ... |

FIG 7

PACS UF

| Nr. | Process unit | UA | ZD | DV |
|---|---|---|---|---|
| 1 | PACS Transfer | always | t=DV/ input soeed | - |

FIG 8

Data network UF

| Nr. | Process unit | UA | ZD | DV |
|---|---|---|---|---|
| 1 | Data transfer | always | t=DV/ bandwidth | - |

FIG 9

| Nr. | Process unit | UA | ZD | DV | BG | SD |
|---|---|---|---|---|---|---|
| | | | Raw data acquisition unit (Volume coverage = 30 cm; rotation time = 0.5 s) | | | |
| 1 | Raw data acquisition | Intestine | t = volume coverage/ rotation time | 1 GB | 512 x 512 | 0.6 mm |
| | | ... | ... | ... | ... | ... |

| | Pre-processing (Pre-processing performance = 2 GB/s; data stream performance = 170 MB/s) | | | UF |
|---|---|---|---|---|
| Nr. | Process unit | UA | ZD | DV |
| 1 | Raw data pre-processing | Intestine | t = data volume/pre-processing performance | - |
| | | ... | ... | - |
| 2 | Raw data forwarding | Intestine | t = data volume/data stream performance | - |
| | | ... | ... | - |

FIG 11

| | Raw data storage (reception performance = 200 MB/s; storage performance = 10 MB/s) | | | UF |
|---|---|---|---|---|
| Nr. | Process unit | UA | ZD | DV |
| 1 | Reception | Intestine | t = data volume/ reception performance | - |
| | | ... | ... | - |
| 2 | Transmission to the local data bank | Intestine | t = data volume/ storage performance | - |
| | | ... | ... | - |

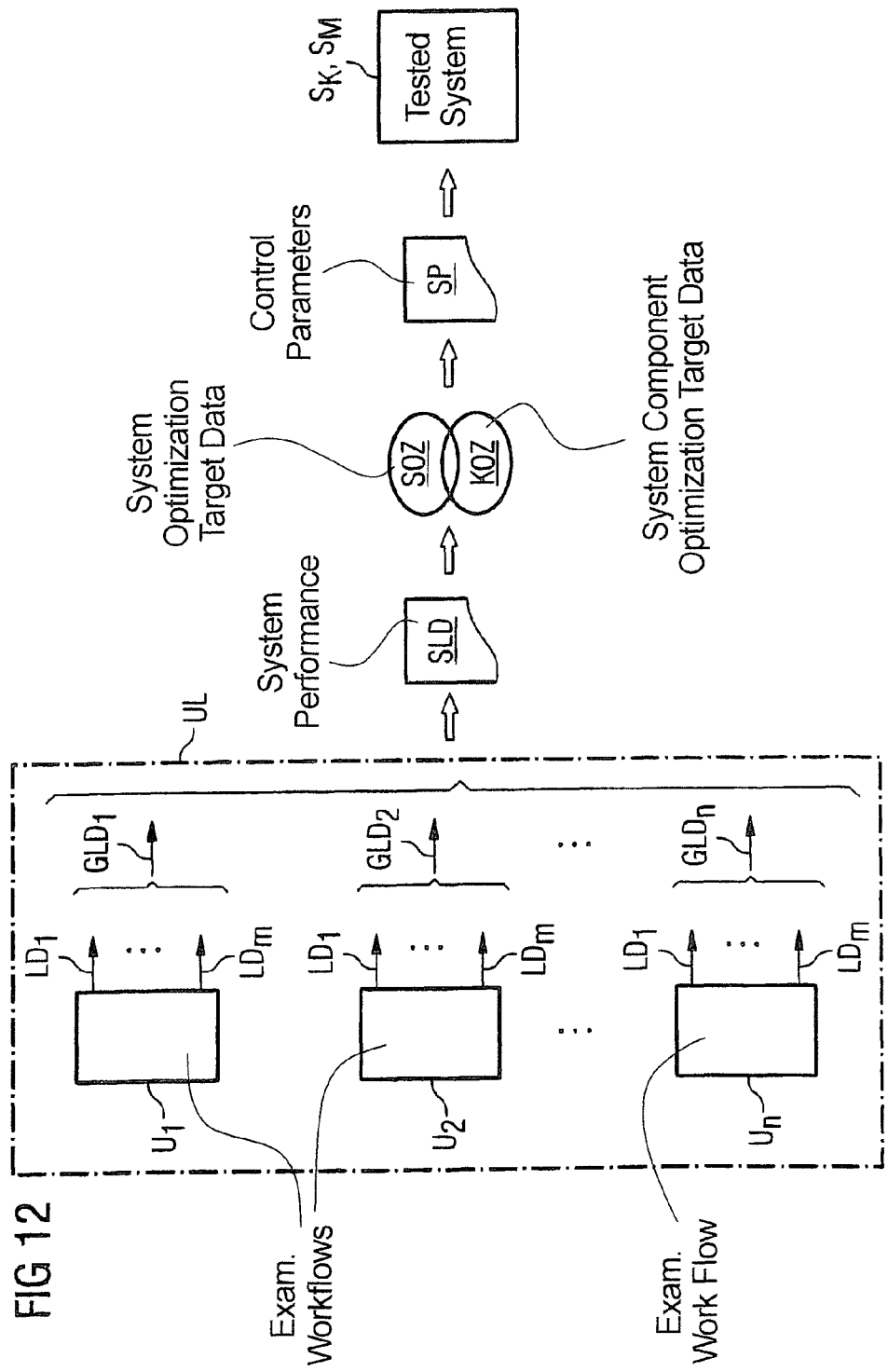

METHOD FOR TESTING AND CONTROLLING WORKFLOWS IN A CLINICAL SYSTEM AND/OR COMPONENTS THEREOF

BACKGROUND OF THE INVENTION

1. Field of the Invention

The invention concerns a method to test a clinical and/or medical-technical system with a number of system components as well as a method for controlling medical-technical examination workflows in such a system.

2. Description of the Prior Art

Large medical apparatuses (also called "modalities") such as computed tomography systems, magnetic resonance tomography systems, x-ray systems, ultrasound systems, angiography systems and similar apparatuses are extraordinarily complex medical-technical systems. Such systems include a number of quite different system components. In particular, different hardware components such as data acquisition devices, cooling devices, control computers etc. are present in such systems as well as software components such as different types of image evaluation software or applications with special monitoring and control processes. Moreover, many of these system components in turn encompass a number of sub-components. For example, a data acquisition component normally has a signal generation device (for example a radio-frequency system in magnetic resonance tomography or an x-ray radiator in computed tomography) as well as a suitable detector device. Such medical-technical systems can in part be individually assembled from various components, and the individual components must be appropriately matched to one another and correspondingly adjusted in order to achieve an optimal system performance.

The same applies in macroscopic consideration for the employment of such medical-technical systems within their use environment, i.e. within a clinical system. As used herein a "clinical system" means an arrangement that includes as a system component a medical-technical system as described above and at least some of the further components required for operation of the medical-technical system in a clinical workflow, such as preparation rooms, post-processing rooms and in particular peripheral apparatuses and systems such as workstations, networks, printing stations etc. As with the medical-technical system itself, it is also true for such a clinical system that an optimal performance can be achieved only with an optimal selection and settings of the system components under consideration of the respective other components present in the system. An optimal setting of such a clinical system exists when a sufficiently high patient throughput is achieved and thus the wait times for the patients, the downtimes of the apparatuses, and unnecessary wait times for personnel are minimized. Nevertheless, it must be possible to handle emergency situations quickly and without problems and necessary system maintenance cycles of individual components must be preserved, for safety reasons as well as to ensure the technical quality of the examination results.

Generally, new modalities are specified with regard to their performance in the development laboratories on the basis of experimental values, and corresponding tests are conducted. In order to evaluate the possible patient throughput in such a medical-technical system, variations of quite different performance-determining parameters must be taken into account. The interaction of all variants is very complex. An exact conclusion of how such a medical-technical system behaves in the clinical environment is generally not possible. Moreover, such tests are relatively time-consuming and costly due to the number of persons involved therewith.

SUMMARY OF THE INVENTION

An object of the present invention is to provide a simple and cost-effective method to test a clinical and/or medical-technical system that supplies reliable conclusions about the clinical and/or medical-technical system, particularly about its performance.

A basis of the inventive test method is that medical examination workflows in the clinical and/or medical-technical system are simulated within the test. The simulation of a medical examination workflow includes the following steps.

A process workflow plan is initially selected from a number of process workflow plans, dependent on an examination task of the appertaining examination workflow. Each process workflow plans includes a number of process units interlinked with one another, for example linked in series or in another manner. At least one system component of the clinical and/or medical-technical system is associated with these respective process units. Furthermore, an input parameter set, an output parameter set and at least one transfer function, which translates the parameter values of the input parameter set into the output parameter values of the output parameter set, are associated with the process unit. This transfer function is dependent on the examination task and/or the associated system components of the clinical and/or medical-technical system.

In a further step, a number of output parameter values and/or performance data for the individual process units are then respectively determined from a number of input parameter values for the appertaining process units on the basis of the transfer function that is associated with the appertaining process unit, dependent on the examination task and/or the associated system components of the clinical and/or medical-technical system. Respective output parameter values of a process unit are thereby used as input parameter values for a subsequent process unit within the process workflow plan.

This means that a number of start input parameter values are fed into a first process unit in the method. These start input parameter values are then converted by the process unit into output parameter values according to the transfer function associated with the process unit, and according to the process workflow plan these output parameter values then pass into the subsequent process unit which generates output parameter values therefrom and then passes these values to the following process unit until, ultimately, the last process unit within the process workflow plan is reached. The process units respectively form individual sub-processes of the examination workflow that run on the respectively-associated system components. The performance data determined with regard to a specific process unit thus are also performance data of the associated system component.

In principle it is possible for various process units to be connected in parallel. For example, two different process units can be started whose output parameter values are in turn passed to a common subsequent process unit that incorporates the output parameter values of the aforementioned process units as input parameter values. A number of process units connected in parallel can likewise be downstream from one process unit.

The input parameter values or output parameter values are values of the parameters defined in the input parameter set or output parameter set. It is not necessary for all input parameter values of an input parameter set to be transferred to a process unit, nor is it necessary for this process unit supplies output parameter values for all parameters of the output parameter set. The transfer function, the input parameter set and the output parameter set are, however, defined so as to be adapted to one another such that, insofar as a process unit receives values for specific parameters of the input parameter set, it can convert these into corresponding output parameter values. A "conversion" of input parameter values into output parameter values in principle can involve a simple through loop of the values, meaning that the values are passed on unchanged. This depends on the respective process unit or the associated system components.

The performance data in for each process unit can be determined by means of the transfer function. The performance data themselves can also be viewed as a type of output parameters and be correspondingly further processed. In the inventive test method, precise performance data can be acquired relatively simply and quickly, even from very complex medical-technical systems. In particular the expected clinical environment of a medical-technical system can be taken into account by the examination workflows in the associated clinical system being simulated within the test with the medical-technical system being a component of the clinical system. The method can run almost completely automatically, such that—in contrast to typical test methods—the time cost for the persons or evaluators associated with the test is relatively low. Moreover, not only performance data about the individual process units or system components within the clinical environment, but also performance data of the complete clinical system (which includes a number of medical-technical systems as system components) can be acquired with the inventive test method.

In this manner it can be established whether the performance of the total system can be improved, possibly by changes to system components of the clinical system other than the modalities, for example by a different assignment of preparation rooms and post-processing rooms, change of the network or creation of additional computer capacities or by changing existing process workflows. When, for example, a specific modality is replaced by a new modality within a clinical system, the possibility exists for an increase of the total performance of the system dye to the new modality, insofar as corresponding further components of the system or process workflows are changed. These very often unrealized capacity improvement possibilities are revealed with the aid of the test method and can be appropriately implemented.

The transfer functions can be formed in various manners. For example, they can be constants for some process units and for specific system components. A specific output parameter value is then always generated by this process unit, independently of the input parameter value. Alternatively, the transfer function can be described by a more or less complicated function equation. For example, it can be a simple factor with which the input parameter value is multiplied.

The determination of the transfer function of a process unit that is dependent on a specific system component can ensue on the basis of measurement data that were collected at the appertaining system component and/or at one or more system components similar to this. "Similar system components" means system components that are designed in the same or a similar manner as the appertaining system component and/or that serve the same purpose. It is only important that the measurement data which were collected at such a similar system component are also significant for the appertaining system component of the system to be tested. In this manner, measurement data already acquired on existing systems can be used for the inventive test. For example, test results from simple tests (in particular functional tests as to whether a specific system component can ensure a specific performance at all) can be incorporated into the inventive, more complex system test.

The transfer function of a process unit preferably is stored in the form of a table defined for a specific system component. A time duration for the appertaining process unit and/or an output data volume of the process unit is defined in this for each examination task, for example via a function equation, a constant etc. In particular the time duration that a process requires on the individual process units as well as the output data volume output in the respective process units are important for the performance of the system. The time duration is among the most important performance data, and the output data volume is normally transferred to the subsequent processing unit as an input data volume, with the load and the time duration of this subsequent process unit often being strongly dependent on the output data volume. The time duration at the individual system components and the output data volume are thereby particularly important performance data or output parameters.

As described above, according to the invention a system component of the system is associated with each process unit. This can be either a specific system component when, for example, only this system component is suitable for the appertaining process unit or when only one system component of a specific type is available at all. Alternatively, an arbitrary system component composed of a group of suitable system components can in principle be associated with the process unit. An example of this is a clinical system or a clinic in which only one magnetic resonance tomography apparatus but multiple computer tomographs are available. A specific system component (namely the individual magnetic resonance tomography apparatus of the system) must then be associated with a process unit that represents the data acquisition given a magnetic resonance acquisition. Any of the computed tomography apparatuses available in the clinic can be associated with a process unit which represents the data acquisition for a computed tomography acquisition.

In a clinical system it necessarily occurs that such a system component is already blocked by another process, for example is used for other examinations, or that the system component is faulty. It is likewise also possible that suitable system components are no longer currently available from a group of system components. In this case, the examination workflow cannot be continued. In a simulation, an examination workflow to be simulated is therefore advantageously blocked by the appertaining process unit as long as the determined system component is not available, or no system component from the group of system components is available for associated with the appertaining process unit. The corresponding wait time during which the process unit is blocked is then advantageously protocolled and/or output as a type of performance data of this process unit, such that downtimes that arise due to such blockages can also be revealed and possibly reduced.

It is a similar situation in a real examination workflow, wherein one or more persons are necessary for most processes. For example, given the data acquisition on a modality an operator (normally an MTRA) must always be present. In some cases, multiple people can also be necessary, for example an MTRA and a radiologist. In other process units, for example in a process unit that the task of preparation of the patient for the examination, a nurse is required. In other process units, for example for a report generation process (reporting), only a radiologist is required. For some process units it may be that a very specific person is required; for other process units it is merely necessary to associate one person from a specific personnel group (for example an arbitrary MTRA, an arbitrary radiologist or an arbitrary nurse).

An examination workflow can also be blocked by the absence of a person. An examination workflow to be simulated can be blocked by the appertaining process unit as long as a specific person is not available, or if no person from a designated group of persons is available for association with the respective process unit. This means that the examination workflow is also simply halted at the appertaining process unit in such a case, and the wait time is protocolled until a/the suitable person is finally associated with the process unit. These wait times can also be output and/or processed as performance data.

Furthermore, in reality the performance that is achieved at an apparatus or in a specific process unit can also depend on the respective person who is associated with thus process unit. It is thus possible for a specific MTRA with a longer employment experience to conduct a necessary examination significantly faster than an MTRA who has only a short employment experience. This applies even more for processes that are significantly dependent on personnel such as, for example, for a finding (medical assessment). In order to take this personnel dependency into account, a person with a specific personnel value is respectively associated with the appertaining process units. The transfer function associated with the process unit is then dependent on the personnel value. For example, the transfer function or the part of the transfer function which calculates the time duration in the respective process unit contains a constant factor that is greater the less employment experience that the person has. Process units in which less experienced persons are participating thus automatically take longer than process units with which a very experienced person is associated.

Furthermore, disturbance variables for a system component or person associated with a process unit can be detected which ultimately influence the transfer function of the process unit. Typical disturbance variables for a specific system component would, for example, be tendency towards error, maintenance cycles etc. The basis data to determine such interference quantities, for example, can be measured in already-existing systems. The influencing of the transfer function of the process unit by the disturbance variable is advantageously realized such that an interference function for the appertaining process unit is determined on the basis of the disturbance variable, which interference quantity is linked with the transfer function of the process unit. A typical example of this is a slowdown of a process because the performance of the associated system component is reduced due to the interference. For example, the part of the transfer function which is responsible for the determination of the time duration can be multiplied with a delay factor to represent this case.

As described above, medical examination workflows in a clinical system can be simulated with the inventive method, which clinical system comprises as system components at least one modality as well as a number of peripheral system components, for example preparation rooms, data networks, data post-processing devices or information sub-systems such as RIS (radiology information systems) or PACS (picture archiving and communication system). It is likewise also possible to simulate medical examination workflows within an individually-considered medical-technical system, i.e. within an individual modality. Such a medical-technical system should have as a component at least one data acquisition component, for example a scanner or another measurement value acquisition device. In addition to this, the medical-technical system can have further system components like a control device (control console) for the modality, storage devices such as raw data memory and image data memory and image reconstruction devices or raw data pre-processing devices etc.

For more complex process workflows it is possible to combine multiple process units into a superordinate process unit as sub-process units. This means that a process unit can in turn include a number of sub-process units as a part of a process workflow plan. For example, a process unit that represents an image data acquisition process can thus comprise a topogram process unit and a scan process unit. A process unit that represents an image data processing process can comprise a pre-processing process unit and an image reconstruction process unit. A process unit that represents the finding can comprise a read process unit (reading workflow) and a report process unit (reporting workflow).

This approach has the advantage that, in existing "test tools" with which examination workflows can be simulated in the inventive manner, individual process units can very easily be replaced at a later point in time with "sub-processing units" which describe the real process in more detail. This means that, for example, a first version of a suitable test tool can initially be created with which the inventive method can be implemented in a relatively rough manner. As soon as new data for individual system components are then available, suitable sub-process units can then be created on the basis of these data, which sub-process units more exactly represent the sub-processes of the examination workflow reproduced by existing process units.

Within a clinical system, the parts of an examination workflow that concern the modalities (i.e. the medical-technical systems) can in particular be represented in a very detailed manner by process units with which the individual components of the appertaining medical-technical system are respectively associated. The individual medical-technical systems and the clinical system as a whole can be simultaneously considered in this manner.

The performance data of the individual process units (and thus of the associated system components) of the process workflow plan that are acquired in the simulation of an examination workflow are additionally linked with one another in order to obtain overall performance data of the examination workflow. For example, the time durations necessary at the individual process units can be added together in a suitable manner in order to thus obtain the total passage time for the entire examination workflow. It can likewise be determined how often particular components or persons have led to blockades within an examination workflow or were themselves blocked.

To test the clinical and/or medical-technical system, a number of examination workflows established according to a predetermined examination list (work list) are preferably simulated. Such an examination list can precisely provide which examination workflows are to be executed when with which examination tasks, in particular in which order (successively, in parallel, offset in parallel etc.). The overall performance data and/or the performance data of the individual process units that are acquired in a test of the clinical and/or medical-technical system given the examination workflows simulated according to the examination list are thereby particularly preferably linked with one another to determine system performance data.

All performance data, namely the performance data of the process units and the overall performance data of an examination workflow and the system performance data, can be graphically output in suitable form so that the operator very easily receives an overview of possible weak points of the system and can accordingly find a remedy.

The total simulation can be implemented with suitable software (i.e. with a suitable program code) on any sufficiently-powerful computer. The individual process units (which represent various sub-processes within an examination workflow) with which specific system components are associated are realized in the form of program modules, for example as software subroutines. The input parameter sets and the output parameter sets can respectively form the interfaces between the program modules. Given the operation of such a test tool, the operator preferably has the possibility to define or to vary input parameter sets, output parameter sets and (if applicable) also transfer functions. In particular the operator has the possibility to vary the input data in the simulation as well as framework conditions of the system such as the personnel number, possible disturbance variables for the most varied components, etc.

System optimization target data and/or system component optimization target data are particularly preferably automatically determined on the basis of the performance data and/or the overall performance data and/or the system performance data. This means that automatic suggestions as to how the system and/or the individual components can be optimized are automatically developed within the method.

In the inventive method for controlling medical examination workflows in a clinical and/or medical-technical system with a number of system components networked among one another, control parameters for the clinical and/or medical-technical system and/or its system components can then be determined using the determined system optimization target data and/or system component optimization target data. These control parameters can be automatically transferred to the clinical and/or medical-technical system or, respectively, the appertaining system components. A typical example for this is that within such a simulation it is detected that, within a network of a clinical system, the computer capacity for specific process units is not sufficient and is thereby leading to unnecessary delays or blockades, and that on the other hand specific system components that are associated with other process units are not being operated at full capacity. By suitable adjustment of control parameters of the appertaining system components and/or of the network, the free computer capacities can then be provided for the process units that run unnecessarily slow. The performance of the total system can be increased automatically and without additional costs in this manner.

The above object is also achieved in accordance with the present invention by a computer-readable medium encoded with program code that causes a computer, into which the computer-readable medium is loaded, to execute a method as described above.

DESCRIPTION OF THE DRAWINGS

FIG. 6 shows a table with transfer functions for a display unit as a system component of a clinical system.

FIG. 7 shows a table with a transfer function for a PACS as a system component of a clinical system.

FIG. 8 shows a table with a transfer function for a data network as a system component of a clinical system.

FIG. 9 shows a table with transfer functions for a DMS as a system component of a clinical system.

FIG. 10 shows a table with transfer functions for an IRS pre-processing module (IRS=image reconstruction system) as a system component of a medical-technical system.

FIG. 11 shows a table with transfer functions for a raw data storage as a system component of a medical-technical system.

FIG. 12 is a schematic representation of a workflow of an inventive control method for controlling medical examination workflows in a clinical and/or medical-technical system, including the inventive test method.

DESCRIPTION OF THE PREFERRED EMBODIMENTS

Both clinical and/or medical-technical systems are capable of being tested with the aid of the inventive test method, by examination workflows being simulated within the appertaining systems.

Figure 1:
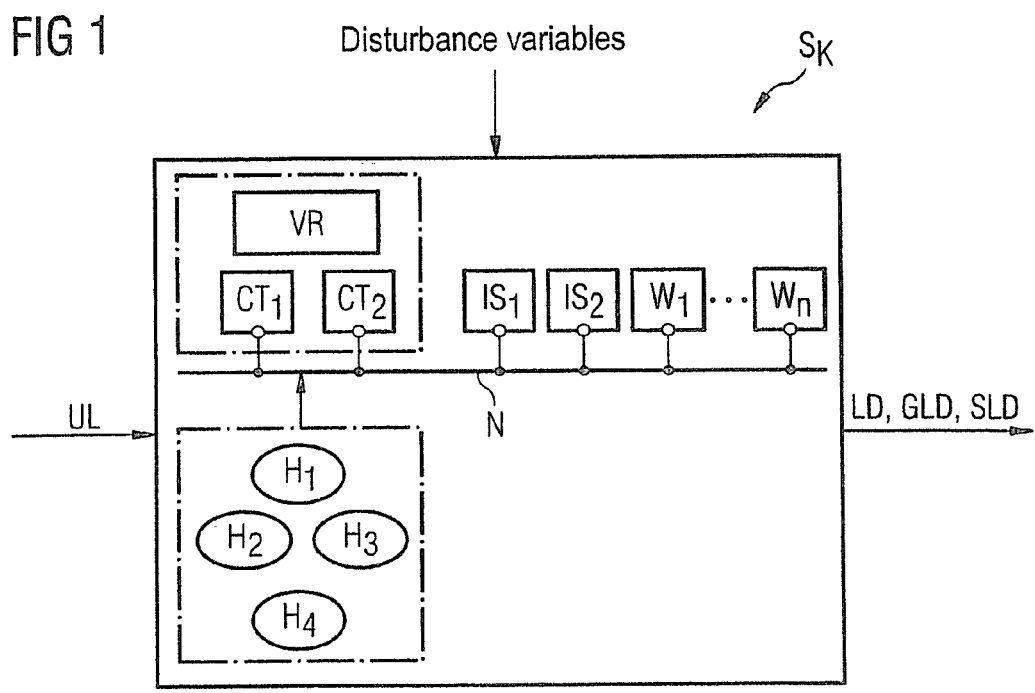
FIG. 1 is an overview representation of a clinical system with a number of system components.

FIG. 1 gives an overview of a clinical system $S_K$. As can be seen in

FIG. 1, a clinical system $S_K$ has one or more modalities $CT_1$, $CT_2$. The shown example is a clinical system $S_K$ with two modalities $CT_1$, $CT_2$, namely two computed tomography apparatuses $CT_1$, $CT_2$. As medical-technical systems, these computed tomography apparatus $CT_1$, $CT_2$ can likewise be considered in greater detail and inventively tested by simulations. This can subsequently described using FIG. 2.

In the test of a clinical system $S_K$, however, the focus also includes the analysis of the other participating system components, i.e. not only on the medical-technical systems, which here are initially considered as "black box" system components. In addition to the modalities $CT_1$, $CT_2$, the clinical system $S_K$ normally further comprises one or more preparation rooms VR in which the patients are prepared for the examination. Moreover, for example, one or more information systems $IS_1$, $IS_2$ (here a PACS (picture archiving and communication system) $IS_1$ and an RIS (radiology information system) $IS_2$) as well as a plurality of workstations $W_1 \ldots W_n$ and a data network N that connects all system components among one another belong to such a clinical system. The personnel, who are grouped in a number of personnel groups $H_1$, $H_2$, $H_3$, $H_4$, are likewise necessary in a clinical system. The personnel group $H_1$ comprises the MTRAs, the second personnel group $H_2$ includes the radiologists, the third personnel group $H_3$ includes care personnel and the fourth personnel group $H_4$ includes cleaning personnel.

In an inventive test of a clinical system, the performance and the capacity of all system components, i.e. both the purely technical components (such as the modalities $CT_1$, $CT_2$, the information systems $IS_1$, $IS_2$, the workstations $W_1, \ldots, W_n$ or the network N) and the non-technical components (such as, for example, the preparation room VR) are of interest due to the interactions therebetween. The personnel usage and the other processes within the clinical system (such as the patient residence time and the workflow of the patient preparation) are also important for the individual simulations. These influencing variables can vary arbitrarily. For example, in addition to technical deficiencies of the components, effects that are caused by additional (unnecessary) or lacking personnel can thus be easily detected via the simulations within the inventive test method.

An examination list UL, in which the determined examination workflows $U_1, U_2, \ldots, U_n$ with their respective own examination tasks UA (such as, for example, "computed tomography of the intestine", "computed tomography of the head", "examination of the lung" etc.) are codified in the form of workflows, form the input for a test. The progression of a possible examination workflow is subsequently explained in further detail using FIG. 3.

The test delivers specific performance data as an output. Within this category is information about bottlenecks, data volumes, resource utilization, pass times, times per patient, number of the patients per time unit, costs and similar data. These performance data can be acquired for individual processing units or for system components. The total performance data for the complete examination workflows, or system performance data for the complete system, likewise can be acquired after a simulation with multiple examination workflows.

Disturbance variables such as a failure of resources, i.e. the failure of specific system components, necessary cleanings or patient complications (i.e. dependent upon contrast agent administration, etc.) can be taken into account in the simulation as additional data. Furthermore, work time organization data with regard to the personnel, such as break rules, shift models etc. also can be taken into account.

Figure 2:
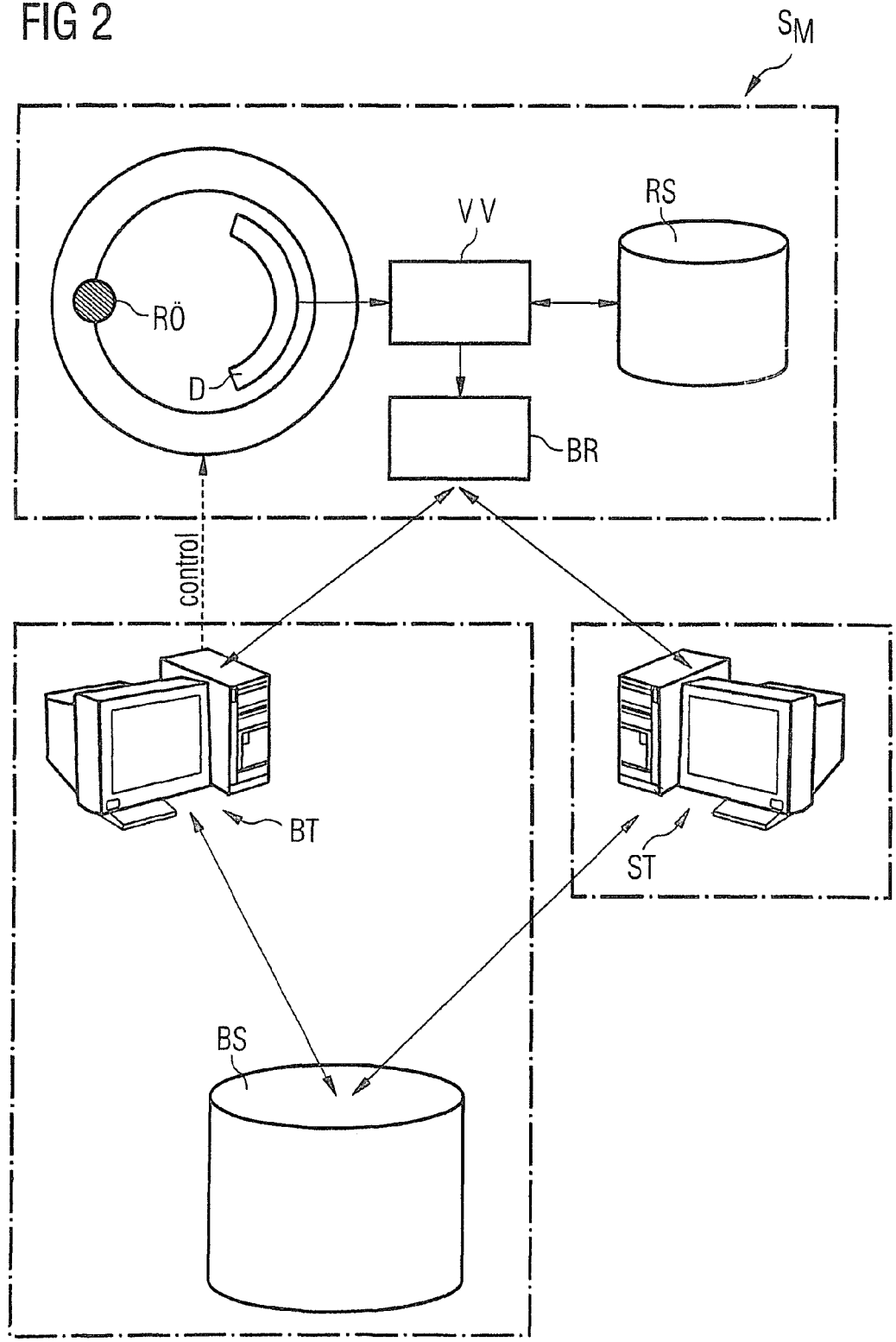
FIG. 2 is an overview representation of a medical-technical system with a number of system components.

FIG. 2 shows a detailed overview of the individual components of a medical-technical system $S_M$, i.e. of an individual modality, here in the example a computed tomography apparatus. A main component here is the raw data acquisition device RA, composed of a gantry with an x-ray source RÖ and a detector D. The raw data are acquired in a typical manner with the aid of this raw data acquisition device RA. The raw data are then transferred to an IRS pre-processing component VV that stores the data in a raw data storage RS and/or transfers them to an IRS image reconstruction unit after the preparation-processing.

These aforementioned components are controlled through an operating terminal BT (also called a "control console"), for example a Navigator® commercially available from Siemens. The post-processing also can be controlled and the reconstructed image viewed with the aid of the Navigator®. In an overview scan (known as a topogram), generated images also can be used in order to plan the subsequent examinations. The viewing of the images and the controlling of the post-processing, moreover, can be implemented with a viewing terminal ST, for example the Wizard® also commercially available from Siemens. Direct control of the raw data acquisition system, however, is not possible with the Wizard®. The finished images can then be stored in an image data storage BS and be retrieved there again.

At this point, it should be noted that a medical-technical system $S_M$ does not necessarily have to contain all of these cited components. For example, the display terminal and the image data storage can be considered as additional components which, for example, are included only in the framework of the simulation of a clinical system but are not considered as a part of the actual modality. The medical-technical system likewise can include other system components that are not shown, for example specific software applications. Furthermore, the sub-components of the shown system components can be taken into account in order to be able to represent specific process workflows in more detail. This means that it is in principle also possible to deconstruct individual components of the shown components even further into sub-components and to respectively, individually take these into account in the simulation, and with these system components to represent running parts of the examination workflow as individual process units within the simulation or the process workflow plan.

In the test of a medical-technical system $S_M$, i.e. a modality, it the system parameters as well as the system components that influence the performance of this modality should be made transparent to a particular degree. In order to obtain a conclusion regarding the total performance of the modality, however, the system properties are simulated in combination with the clinical workflow. This means that the test of such a medical-technical system $S_M$ preferably ensues within a test of the complete clinical system $S_K$. For this purpose, for the representation of the examination workflows in a simulation the more complex medical-technical systems are considered instead of the black box components (similar to as shown in FIG. 2), which is different than is shown in FIG. 1.

For example, in addition to relevant disturbance variables in such a medical-technical system, necessary service applications, uncooperative patients, system backlogs or (in the case of a computed tomography or x-ray apparatus) the required cool-down time of the x-ray tube upon an overheating, can be embodied in the simulation.

Figure 3:
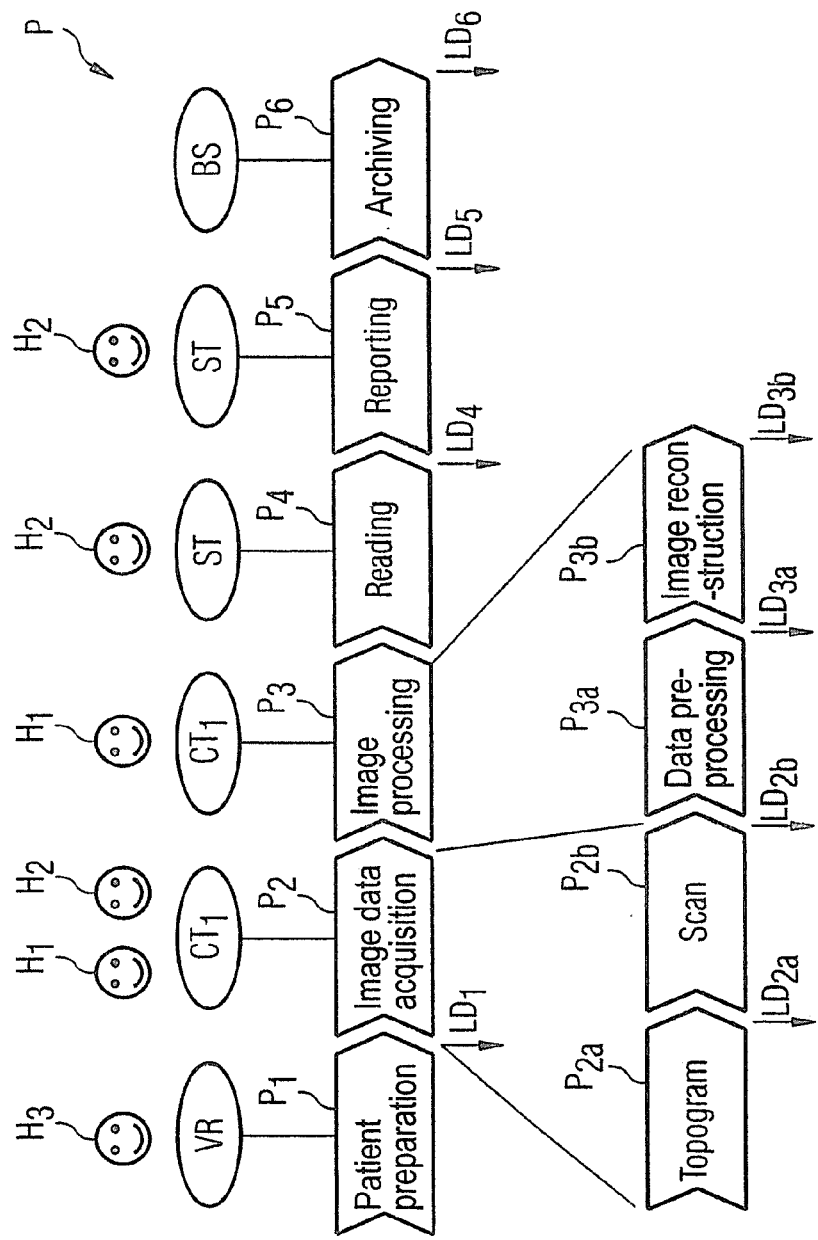
FIG. 3 is a schematic representation of an embodiment of process workflow plan to represent an examination workflow.

In a very simplified manner, FIG. 3 shows how an examination workflow within a clinical system $S_K$ can be represented by a process workflow plan P that includes a number of process units $P_1, P_2, P_3, P_4, P_5, P_6$.

The first process unit $P_1$ represents the patient preparation. This process unit $P_1$ is accordingly associated with the preparation room VR as a system component.

The second process unit $P_2$ represents the actual image data acquisition. The image data acquisition is associated with the computed tomography apparatus $CT_1$ as a system component. This process unit $P_2$ also can be represented in more detail by two "sub-process units" $P_{2a}, P_{2b}$, with the first process unit $P_{2a}$ corresponding to the generation of a topogram and the second process unit $P_{2b}$ corresponding to the subsequent actual scan to implement the acquisition. In this case, the computed tomography apparatus $CT_1$ is associated with both process units $P_{2a}, P_{2b}$ as a system component.

A process unit $P_3$ that represents the image processing follows after the image data acquisition $P_2$. The computed tomograph apparatus $CT_1$ is likewise associated with this process unit $P_3$ as a system component. This process unit can also be subdivided into finer process units, for example into a first process unit $P_{3a}$ that represents the data pre-processing and a second process unit $P_{3b}$ for the image reconstruction. In this case, if a corresponding medical-technical system with a number of system components (similar to the representation in FIG. 2) were considered instead of the computed tomograph apparatus $CT_1$ as a "black box", the pre-processing unit VV could be associated with the first process unit $P_{3a}$ and the image reconstruction unit BR could be associated with the second process unit $P_{3b}$.

A process unit $P_4$ that represents the reading of the images (reading) then follows after the image processing, and a further process unit $P_5$ that represents the generation of the examination report (reporting) follows this process unit $P_4$. A workstation $W_1$ is respectively associated with both process units $P_4, P_5$. Archiving of the images subsequently ensues in the framework of a further process unit $P_6$. The image storage BS is accordingly associated with this process unit as a system component.

As can be seen from the representation according to FIG. 3, people are also associated with most of the process units $P_1$, $P_2$, $P_3$, $P_4$, $P_5$, $P_6$. For example, a person from the group of care personnel $H_3$ is required for patient preparation. An MTRA $H_1$ and a radiologist are necessary in the image data acquisition. The image processing is then implemented by only one MTRA $H_1$, and the reading and the reporting are affected by a radiologist $H_2$. The archiving ensues automatically without a person being associated therewith.

In a simulation of an examination workflow, performance data $LD_1$, $LD_{2a}$, $LD_{2b}$, $LD_{3a}$, $LD_{3b}$, $LD_4$, $LD_5$, $LD_6$ are generated for each of the process units $P_1$, $P_{2a}$, $P_{2b}$, $P_{3a}$, $P_{3b}$, $P_4$, $P_5$, $P_6$. For example, these performance data $LD_1$, $LD_{2a}$, $LD_{2b}$, $LD_{3a}$, $LD_{3b}$, $LD_4$, $LD_5$, $LD_6$ include data as to the respective time durations of each process unit $P_1$, $P_{2a}$, $P_{2b}$, $P_{3a}$, $P_{3b}$, $P_4$, $P_5$, $P_6$, whether there were wait times at the associated system component during this time period, how many patients have been attended to at this system component, etc.

The simulation of an individual examination workflow hereby ensues as follows.

Start parameters are initially provided for the first process unit $P_1$; meaning that parameter values are selected for an input parameter set EPS of the first process unit $P_1$. Output parameter values APW for an output parameter set APS are then determined within the first process unit $P_1$ on the basis of the input parameter set EPS with the specific input parameter values EPW and based on the transfer function UF, which depends on the associated system component and the examination task.

Figure 4:
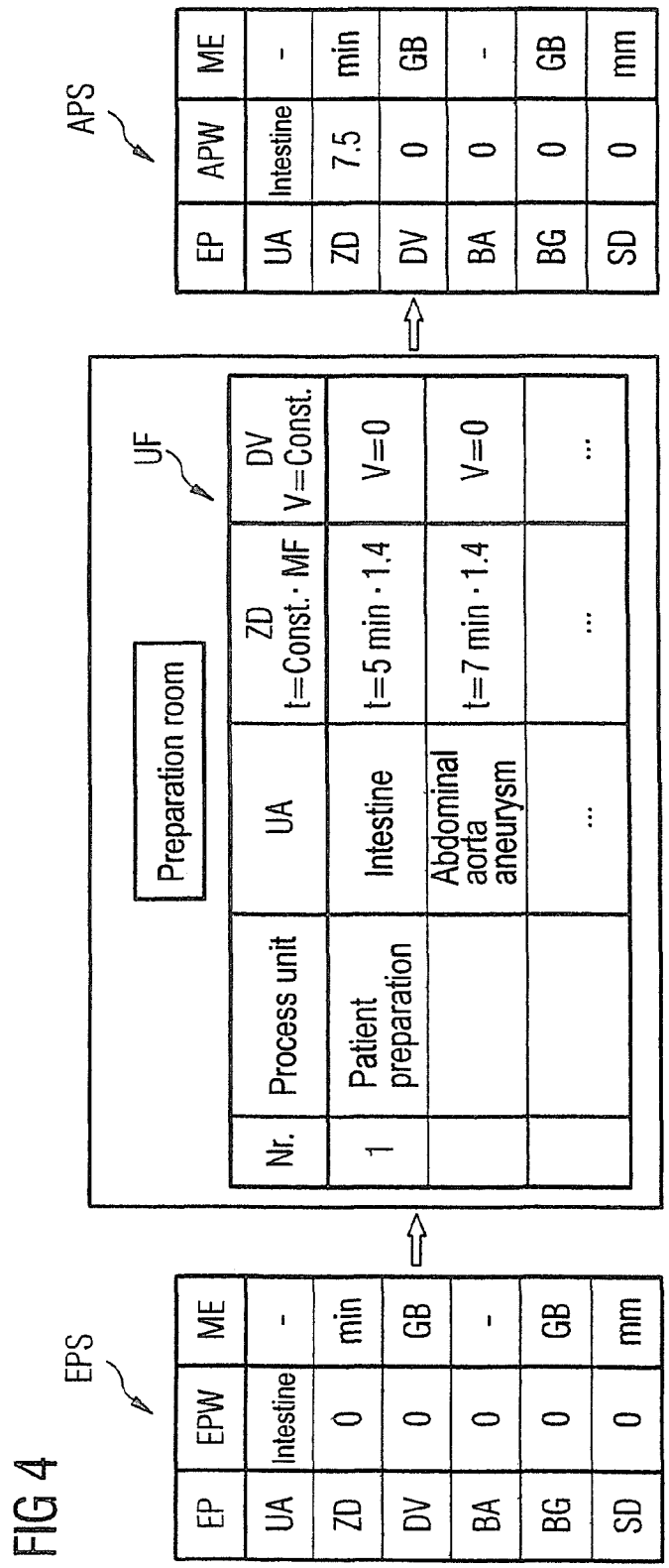
FIG. 4 shows an input parameter set, a table with transfer functions and an output parameter set with a preparation room as a system component of a clinical system.

The input parameter set EPS for the patient preparation which occurs in the preparation room VR is shown in FIG. 4. Among other things, the examination task UA, a time duration ZD, a data volume DV, an image number BA, an image size BG and a slice thickness SD belong here to the input parameters EP of the input parameter set EPS. This is shown in the first column of the table. The associated input parameter value EPW is specified in the second column and the associated measurement unit ME is specified in the third column.

For the input for patient preparation (process unit $P_1$ in FIG. 3), the input parameter set EPS merely includes the examination task UA (here specifically an examination of the intestine) as an input parameter value EPW. It is clear that the examination task UA can be specified significantly more precisely, for example as an "examination of the appendix" or "search for an intestinal cancer". For each of these examination tasks UA or the associated examination workflows, it is precisely established which steps are to be implemented within the individual process units of the associated process workflow plan, which systems components and which persons are necessary for this purpose and how the transfer functions look for the respective process units. These dependencies are stored in the form of tables for the individual system components. For each process unit and each examination task it is established in such a table how the output parameter values for the output parameter set are generated on the basis of the various input parameter values of the input parameter set.

The table for the preparation room VR is shown as an example in FIG. 4, whereby for better presentability here only the transfer functions with regard to the time duration and the data volume are shown. Normally all transfer functions for the other input parameter values EPW (for example for the image number BA, the image size BG, slice thickness SD etc.) are stored in the table insofar as the appertaining parameters are influenced at all at the corresponding system components.

Since only the patient preparation is implemented in this system component VR, there is only one process unit linked therewith. The table for the preparation room VR need include only the transfer functions for the patient preparation process unit $P_1$, however, a number of different examination workflows with various examination tasks exist, for which the transfer function can appear differently. In FIG. 4 only an intestine examination (first line) and the examination of an abdominal aorta aneurysm (second line) are shown as examples. Dependent on the examination task, the time duration that the patient preparation requires is established here. A data volume is not generated at all in this unit, such that a constant data volume V=0 can be set as an output parameter value insofar as the table of the preparation room contains data about the data volume at all. "0 values" for the other unaffected parameters BA, BG, SD of the input parameter set EPS could also be stored in the table in a similar manner. The time duration ZD, which corresponds to a time constant (for example the average value of the times typically required for the preparation given such an examination task) multiplied with a personnel factor MF, is provided by a function according to this table. This personnel factor MF depends on the associated person and reflects the fact that process can run faster or slower with different personnel who have different experiences and routines.

The factor MF can be stored, for example, in a personnel table. For example, the number of the available people, their employment experience and (linked with this) the personnel factor MF can be stored in such a personnel table. An example for this is a list in which it is established that three radiologists with one to two years of employment experience and a factor MF=1, one radiologist with ½ a year experience and a factor MF=1.8, three technicians with more than 2 years employment experience and a factor MF=1 as well as three nurses with employment experience from 6 to 12 months and a factor MF of 1.4, are available. By changing this personnel table, in a test it can be checked as to what extent the overall system is influenced by variation of the personnel (in particular due to a personnel loss) and to what extent these consequences, if applicable, can be at least partially. compensated, for example by different utilization or reorganization of the technical components.

In the example shown in FIG. 4, a preparation for an intestinal examination takes 5 minutes in principle, and a time duration ZD of 7.5 minutes for implementation of the patient preparation is reached by the multiplication with the personnel factor MF=1.4. The value 7.5 is accordingly entered into the output parameter set APS as an output parameter value AP for the time duration ZD.

Within the first process unit $P_1$, which represents the patient preparation, on the basis of the transfer function stored in the table an output parameter set APS is consequently generated as a result of an input parameter set EPS that contains the examination task UA as a single input parameter value EP. This output parameter set APS, the time duration ZD according to the workflow of the first process unit $P_1$ is entered in addition to the "looped through" examination task UA.

This time duration ZD can be transferred to the subsequent process unit as an input parameter and be adapted as part of the performance data $LD_1$.

Figure 5:
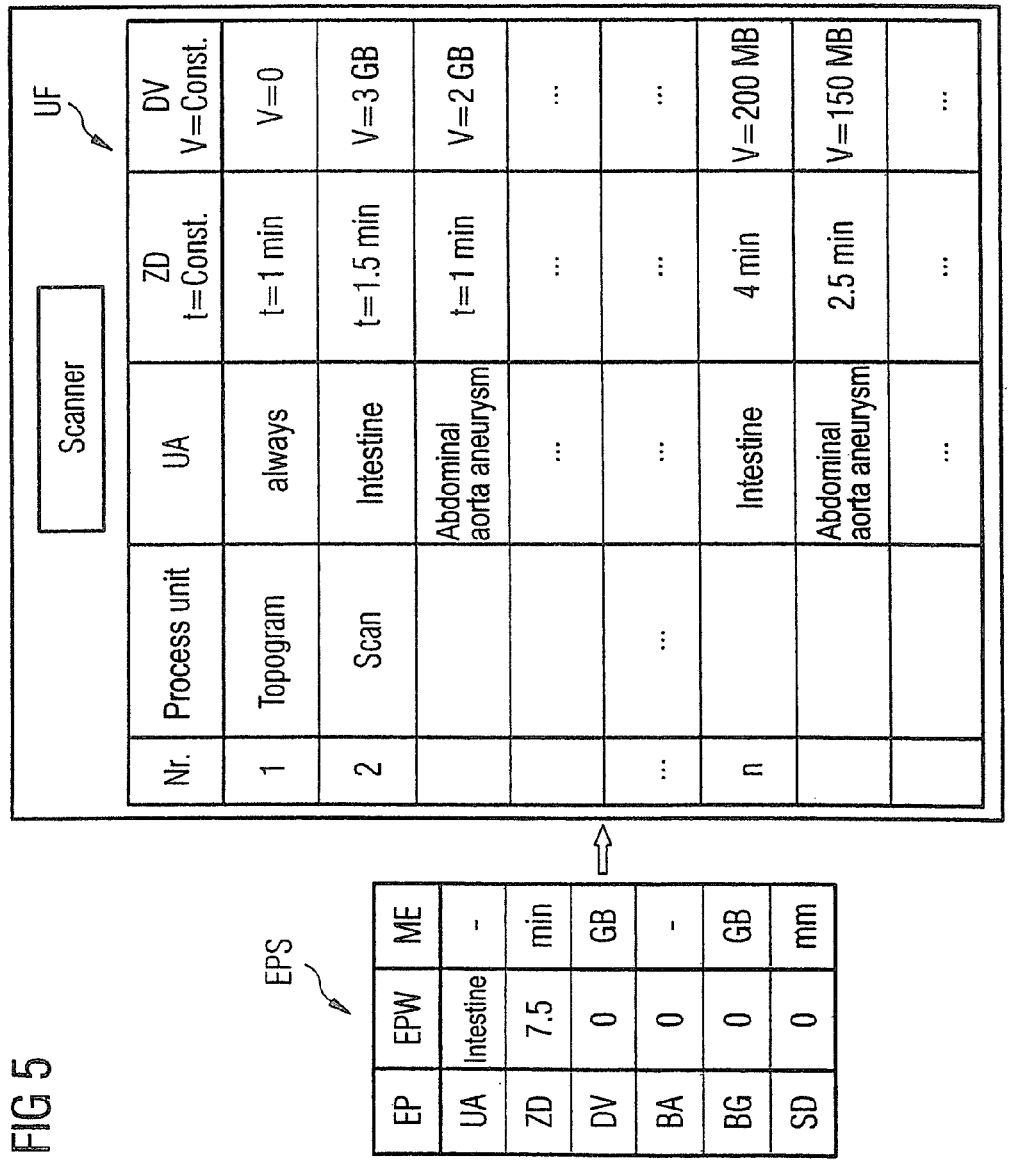
FIG. 5 shows an input parameter set, a table with transfer functions and an output parameter set for a computed tomography apparatus as a system component of a clinical system.

As a further example, FIG. 5 shows a table with the transfer functions UF for various process units that are linked with a modality $CT_1$ as a system component of the clinical system $S_K$. The input parameter set EPS here corresponds to the output parameter set APS in FIG. 4. According to FIG. 3, the next process unit $P_2$ is the image data acquisition, which can also be considered as two sub-process units $P_{2a}$, $P_{2b}$, namely first the generation of a topogram and then the generation of a scan. The computed tomography apparatus $CT_1$ is associated with both sub-process units $P_{2a}$, $P_{2b}$. The transfer functions for the process units $P_{2a}$, $P_{2b}$ "topogram" and "scan" are accordingly, respectively stored in the table for the computed tomography with the associated varying examination tasks UA.

In the shown exemplary embodiment, the examination task UA is irrelevant with regard to the topogram since this process unit $P_{2a}$ here always requires the same time duration of 1 minute. A constant time duration ZD of 1 min. as a transfer function UF is accordingly always found according the process unit "topogram" in the table. A data volume DV which should be conveyed as output parameters to further units is not generated.

This is different for the scan. For the scan, both the time duration ZD and the generated data volume DV are dependent on the examination task UA. Again only an intestinal examination and the examination of an abdominal aorta aneurysm are shown as examination tasks UA as an example.

The computed tomography apparatus $CT_1$, is also required for the further process units, for example for the process unit $P_{2b}$ that represents the image reconstruction. Transfer functions UF for these process units must therefore also be respectively stored in the table, dependent on the examination task UA. This is shown in the lowermost line in the example of an intestinal examination and an examination for abdominal aorta aneurysm.

The computed tomography apparatus $CT_1$, is likewise also necessary for the data pre-processing (process step $P_{3a}$ in FIG. 3). The transfer functions associated with this step, however, not shown in FIG. 4.

For each of the process units $P_{2b}$, $P_{3a}$, $P_{3b}$ specified in the table in FIG. 5, the output parameter set APS is now determined from the respective input parameter set EPS using the data or transfer functions UF stored in the table. This output parameter set APS then becomes the input parameter set for the subsequent process unit, the transfer functions of which are (if applicable) defined again in the same table (but in another line) in order to convert the input parameter set into a corresponding output parameter set for the subsequent process unit. This means that, in a first step corresponding to the process unit $P_{2a}$ that represents the topogram generation, the input parameter set is changed only to the extent that the time duration of 7.5 minutes is increased to 8.5 minutes because the topogram always takes 1 minute according to the transfer function in this simplified example. These output parameter values are then transferred to the next process unit $P_{2b}$ (here the scan) as input parameter values and a new output parameter set is determined according to the transfer function in the table. This output parameter set APS is represented in FIG. 5. In the present task, an intestinal examination, the scan takes 1.5 minutes, such that the total time duration and consequently the time duration output parameter value is 10 minutes. A data volume of 3 GB is generated.

The above example concerns the case where the image data acquisition proceeds in two sub-processes. In principle, it is also possible (as shown in FIG. 3) to represent the image data acquisition as one process, i.e. with less refinement. In this case, the same input parameter set APS would be used and, for example, the transfer functions for the topogram and the actual scan would be merged corresponding to the tasks. This has advantages when, for example, a fixed time is always associated with the topogram in a simple simulation (as shown in FIG. 5). In contrast to this, if the output parameters or the transfer functions within the topogram process unit still depend on further parameters, it is more advantageous to represent the topogram and the actual scan as separate process units.

This correspondingly applies for the image processing process unit $P_3$ as well as for all further process units.

FIG. 6 shows a further example for a transfer function table, here for the process units which use a display unit ST as a system component of the clinical system $S_K$. Constant time durations and constant output data volumes are also specified in this table as simplified transfer functions for the individual process units and examination tasks.

FIG. 7 shows a corresponding table for the PACS as a system component of the clinical system $S_K$. Here there is only the data transfer in the PACS as an associated process unit. The time duration is not a constant, but rather depends on the input data volume which is transferred with the input parameter set as well as on the input speed. A similar dependency is presented for a data network N in the transfer function shown in FIG. 8. The associated process unit is here the data transfer that, independent of the examination task, always leads to a time duration that depends on the input data volume and the current bandwidth of the data network. The input speed of the PACS and the bandwidth of the data network can, for example, be varied during the test or can also depend on other performance data within the simulation.

FIGS. 9 through 11 respectively show examples for tables with transfer functions for various system components of a medical-technical system, here a computer tomograph $CT_1$ according to FIG. 2.

FIG. 9 shows a table with the transfer functions for the raw data acquisition unit RA. There is only one process unit for this, which process unit correspondingly represents the raw data acquisition process. The transfer functions with regard to the time duration ZD and the output data volume DV are stored for this process unit, dependent on various examination tasks. A constant value is set as an output data volume DV dependent on the respective examination task, here a data volume DV of 1 GB given an intestinal examination. The time duration depends on the volume coverage and the rotation time which can be firmly predetermined for the system component as this is specified in the header of the table. These parameters also can be varied in the case of a test in order to establish what influence the variations of these parameters have on the overall performance of the system. Moreover, according to the transfer function, a value of 512×512 pixels for the image size BG and a value of 0.6 memory module for the slice thickness SD are entered into the output parameter set as output parameter values.

FIG. 10 shows an example from a table for the transfer functions of the IRS preparation component. The raw data pre-processing and the raw data forwarding count among the processing units with which the IRS pre-processing component is associated. Various transfer functions are therefore stored again in the table for each of these process units, dependent on the examination task. In the shown exemplary embodiment, in both cases said examination task is again an intestinal examination. A data volume DV is hereby not generated. In the raw data pre-processing, the time duration ZD is dependent on the input data volume and the pre-processing performance. In the raw data forwarding, the time duration ZD is dependent on the input data volume and the data stream performance. Both the pre-processing performance and the data stream performance can again be firmly predetermined for the respective system components, however can also be varied by the operator.

A similar case exists for the system component "raw data storage" RS (see FIG. 2). Here the time duration ZD upon reception of the data depends on the input data volume and on the reception performance. Given the transmission to other databanks, the time duration depends on the data volume and the storage performance, and the reception performance and the storage performance can likewise be definitely predetermined.

The individual tables as shown in FIGS. 7 through 11 are required, for example, when the process workflow according to FIG. 3 is more finely sub-divided into individual process units. In the context of the invention this is possible at any time, as described above.

FIG. 12 schematically shows how the clinical and/or medical-technical system $S_K$, $S_M$ can also be controlled with the aid of the inventive test method in order to achieve an optimization. A number of examination workflows $U_1, U_2, \ldots, U_n$ specified in an examination list $U_L$ are simulated within the inventive test method. Performance data $LD_1, \ldots, LD_m$ are generated in each of these examination workflow simulations. These performance data $LD_1, \ldots, LD_m$ can then be combined into overall performance data $GLD_1, GLD_2, \ldots, GLD_n$ for the appertaining simulated examination workflow $U_1, U_2, \ldots, U_n$. System performance data SLD are then determined from the overall performance data $GLD_1, GLD_2, \ldots, GLD_n$. The actual simulation is concluded with this determination.

Figure 13:
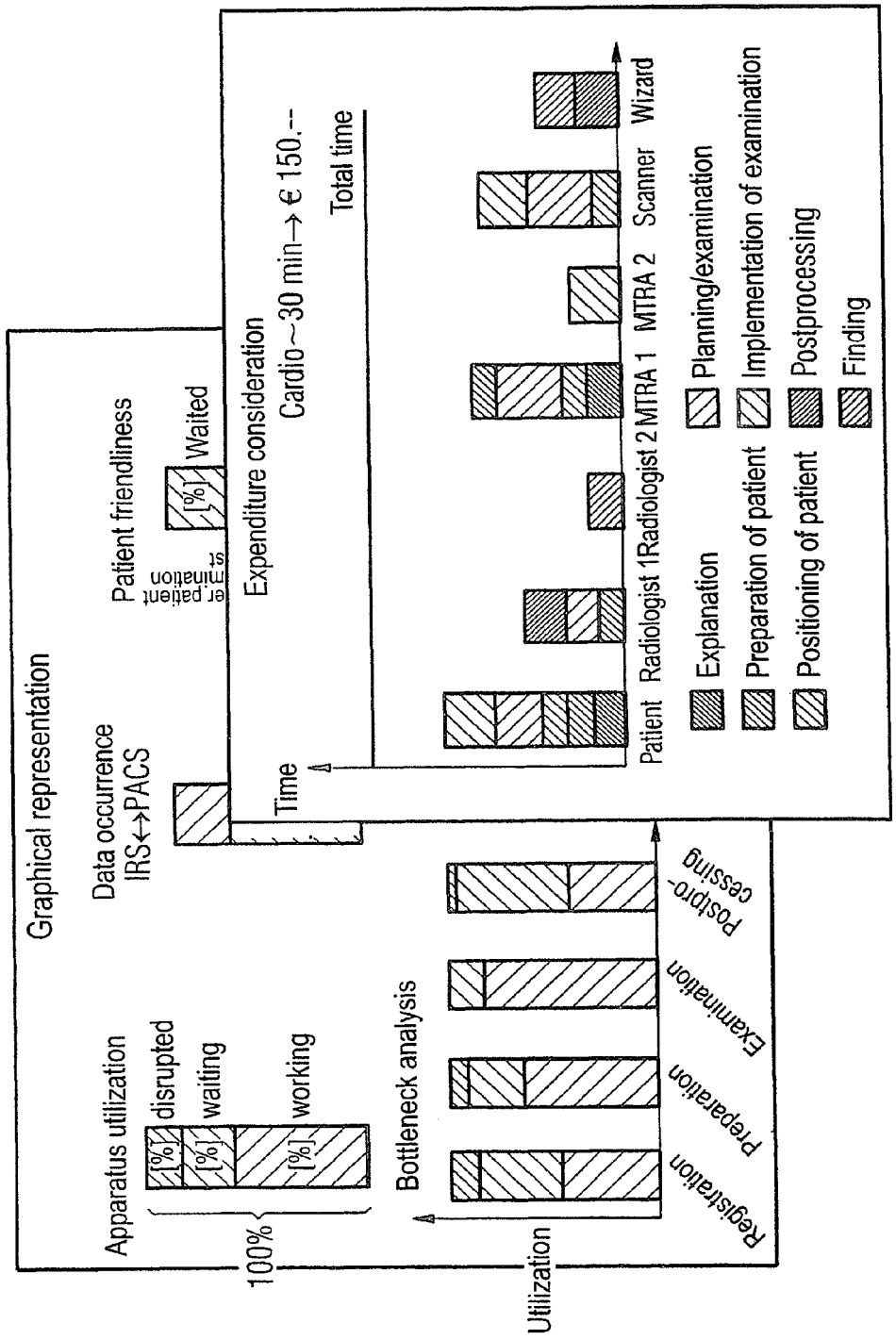
FIG. 13 shows an example of a possible graphical representation of the performance data of a clinical system acquired within the inventive test.

The most varied performance data can then be graphically represented. FIG. 13 shows an example. The total system load, the total data occurrence, the patient friendliness etc. can hereby be shown in correspondingly-prepared form. Moreover, a bottleneck analysis for the individual process units is possible. Information regarding specific questions (such as, for example, the expenditure described for a specific examination workflow) can then be considered via pop-up windows. Using all of these data it is quickly apparent to the operator at which components changes are necessary in order to optimize the system.

As shown in FIG. 12, system optimization target data SOZ and/or system component optimization target data KOZ moreover also can be determined using the system performance data SLD. Control parameters SP can be generated on the basis of these data, which control parameters SP are then used in order to automatically control the tested system $S_K$, $S_M$ such that the intended optimization is automatically achieved.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method for testing a system involved in conducting medical examinations of patients, said system comprising a plurality of system components, said method comprising the steps of:

electronically defining a plurality of simulation process units respectively associated with and representing functioning of at least one of said plurality of system components, by designating, for each simulation process unit, a transfer function that, for at least one simulation input value to that simulation process unit, causes that simulation process unit to produce at least one simulation output value;

for an examination task performable by said system, electronically generating a computer-executable workflow plan that comprises a sequence of a plurality of said simulation process units respectively associated with system components involved in said sequence for executing said examination task, and input parameters to each of the simulation process units in said sequence;

executing said workflow plan in said computer, with each simulated process unit in said sequence in the workflow plan producing at least one output value, dependent on the transfer function thereof, that is used as an input value for a next simulation process unit in the sequence; and emitting a simulation output from said computer, upon completion of execution of the workflow plan, selected from the group consisting of output values for the respective simulation process units in the workflow plan and performance data for the respective simulated process units in the workflow plan.

2. A method as claimed in claim 1 comprising designating the respective transfer functions for the simulation process units from measurement data collected from the system component associated with the simulation process unit or one of said system components similar thereto.

3. A method as claimed in claim 1 comprising electronically storing the transfer function for each simulation process unit as a table defined for the system component associated with that simulation process unit and, in said table, designating at least one of a time duration for participation of that simulation process unit in the examination task and an output data volume produced by the simulation process unit in the examination task.

4. A method as claimed in claim 1 comprising, in simulating said examination task in said computer by executing the workflow plan in said computer, blocking execution of the workflow plan in said computer if any of said input parameters indicates that any of the system components respectively associated with the simulation process units in the workflow plan is not available.

5. A method as claimed in claim 1 comprising electronically associating, with each of said simulation process units, a specified person associated in turn with the system component represented by that simulation process unit, and, in simulating said examination task in said computer by executing the workflow plan in said computer, blocking execution of the workflow in the computer if any of said input parameters indicates that any specified person respectively associated with any of the simulation process units in the workflow plan is not available.

6. A method as claimed in claim 5 comprising, for each specific person associated with a simulation process unit, electronically defining a personnel value and generating said transfer function dependent on said personnel value.

7. A method as claimed in claim 1 comprising, for at least one of said system components, detecting an abnormality selected from the group consisting of a disturbance variable representing a disruption to the functioning of that system component, and an attribute of a person associated with the process unit associated with that system component.

8. A method as claimed in claim 7 comprising automatically electronically generating an abnormality function dependent on said abnormality, and linking said abnormality function with the transfer function of the simulation process unit associated with that system component.

9. A method as claimed in claim 1 comprising testing, as said system involved in conducting medical examinations, a clinical system comprising at least one medical imaging modality and a plurality of peripheral components, forming said system components.

10. A method as claimed in claim 1 comprising defining at least one of said simulation process units as a simulation process unit with a plurality of sub-process units respectively associated therewith and representing functioning of a plurality of components of the system component associated with that simulation process unit.

11. A method as claimed in claim 1 comprising testing, as said system involved in conducting medical examinations, a medical-technical system comprising at least one data acquisition component forming said at least one system component.

12. A method as claimed in claim 1 comprising testing, as said system involved in conducting medical examinations, a medical-technical system comprising at least one data acquisition component and a further system component, forming said plurality of system components, said further system component being a component selected from the group consisting of control devices, storage devices, and image reconstruction devices.

13. A method as claimed in claim 1 wherein said simulation output comprises said performance data for the respective simulation process units in said workflow plan, and comprising the further step of combining the performance data for the respective simulation process units in said workflow plan to generate overall performance data for the workflow plan.

14. A method as claimed in claim 1 comprising selecting the workflow plan, as a selected workflow plan, from an electronic list comprising a plurality of workflow plans that are respectively pre-determined for testing said system.

15. A method as claimed in claim 14 wherein said simulation output comprises said performance data for the respective simulation process unit in the workflow plan, and comprising the further steps of combining the performance data for the respective simulation process units in said workflow plan to generate overall performance data for the selected workflow plan, and linking said overall performance data to that selected workflow plan in said list.

16. A method as claimed in claim 1 wherein said simulation output comprises said performance data for the respective simulation process units in the workflow plan, and comprising the additional steps of combining the performance data for the respective simulation process units in the workflow plan to generate overall performance data for the workflow plan, and graphically displaying at least one of said performance data for the respective simulation process units in said workflow plan and said overall performance data for the workflow plan.

17. A method as claimed in claim 1 wherein said simulation output comprises said performance data for the respective simulation process units in the workflow plan, and comprising the additional steps of combining said performance data for the respective simulation process units in the workflow plan to generate overall performance data for the workflow plan, and automatically electronically determining, in said computer, optimization target data for at least one of said system and a system component in said plurality of system components, dependent on at least one of said performance data for the respective simulation process units in the workflow plan and said overall performance data for the workflow plan.

18. A method as claimed in claim 17 comprising automatically electronically controlling said at least one of said system and a system component in said plurality of components dependent on said optimization target data.

19. A computer-readable medium encoded with program code and being loadable in to a computer in communication with a system involved in conducting medical examination patients, for testing said system, said system comprising a plurality of system components, said program code containing a plurality of electronically defined simulation process units respectively associated with and representing functioning of said plurality of system components, each simulation process unit comprising a transfer function that, for at least one simulation input value to that simulation process unit, causes that simulation process unit to produce at least one simulation output value, said program code causing said computer to:

allow a user interacting with said computer to define a computer-executable workflow plan, for an examination task performable by said system, said workflow plan comprising a sequence of plurality of said simulation process units respectively associated with system components involved in said sequence for executing the examination task and input parameters for each of the simulation process units in said sequence;

simulate said examination task in said computer by receiving input parameters in said computer and executing said workflow plan in said computer dependent on said input parameters, with each simulation process unit in the sequence in the workflow plan producing at least one output value, dependent on the transfer function thereof, that is used as an input value for a next simulation process units in the sequence; and emit a simulation output, upon completion of execution of the workflow plan, selected from the group consisting of output values for the respective simulation process units in the workflow plan, and performance data for the respective simulation process units in the workflow plan.

20. A computer-readable medium as claimed in claim 19 wherein said simulation output comprises said performance data for the respective simulation process units in the selected workflow plan, and wherein said program code additionally causes said computer to generate overall performance data for the selected workflow plan from the performance data for the respective simulation process units, and to generate optimization target data for at least one of said system and a system component in said plurality of components, from at least one of said performance data for the respective simulation process units in the selected workflow plan and said overall performance data for the selected workflow plan, and to control said at least one of said system and a system component in said plurality of system components dependent on said optimization target data.

* * * * *